United States Patent
Boriani et al.

[11] Patent Number: 6,159,211
[45] Date of Patent: Dec. 12, 2000

[54] STACKABLE CAGE SYSTEM FOR CORPECTOMY/VERTEBRECTOMY

[75] Inventors: Stefano Boriani, Bologna, Italy; Mark H. Bilsky; Patrick J. Boland, both of New York, N.Y.; T. Glenn Pait, Little Rock, Ark.; Dawn Abens Lissy, Seven Hills, Ohio; Paul J. Mraz, Cleveland Heights, Ohio; Daniel S. Savage, Brecksville, Ohio

[73] Assignee: Depuy Acromed, Inc., Raynham, Mass.

[21] Appl. No.: 09/177,645

[22] Filed: Oct. 22, 1998

[51] Int. Cl.[7] ..................................... A61B 17/56
[52] U.S. Cl. .................................. 606/61; 606/72; 623/17
[58] Field of Search ................................. 606/61, 72, 73, 606/69; 623/17

[56] References Cited

U.S. PATENT DOCUMENTS

| | | |
|---|---|---|
| 4,696,290 | 9/1987 | Moreland . |
| 4,743,256 | 5/1988 | Brantigan . |
| 4,834,757 | 5/1989 | Brantigan . |
| 4,878,915 | 11/1989 | Brantigan . |
| 4,887,595 | 12/1989 | Heinig et al. . |
| 5,192,327 | 3/1993 | Brantigan . |
| 5,217,461 | 6/1993 | Asher et al. . |
| 5,246,458 | 9/1993 | Graham . |
| 5,257,993 | 11/1993 | Asher et al. . |
| 5,261,910 | 11/1993 | Warden et al. . |
| 5,294,391 | 3/1994 | McMillin . |
| 5,306,309 | 4/1994 | Wagner et al. . |
| 5,397,364 | 3/1995 | Kozak et al. . |
| 5,425,772 | 6/1995 | Brantigan . |
| 5,429,863 | 7/1995 | McMillin . |
| 5,443,514 | 8/1995 | Steffee . |
| 5,522,899 | 6/1996 | Michelson . |
| 5,571,190 | 11/1996 | Ulrich et al. . |
| 5,571,192 | 11/1996 | Schonhoffer . |
| 5,609,635 | 3/1997 | Michelson . |
| 5,658,337 | 8/1997 | Kohrs et al. . |
| 5,665,122 | 9/1997 | Kambin . |
| 5,702,453 | 12/1997 | Rabbe et al. . |

OTHER PUBLICATIONS

Boriani et al., "Scelta Della Strumentazione Nei Tumori Primitivi E Secondari Del Rachide," *Lo Scalpello*, vol. 10, Fascicola 1, pp. 49–51, 1996.

Boriani et al., "En Bloc Resections of Bone Tumors of the Thoracolumbar Spine," *Spine*, vol. 21, No. 16, pp. 1127–1131, 1996.

Boriani et al., "Indicazioni E Risultati Della Vertebrectomia Nel Trattamento DeiTumori Del Rachide Dorso–Lombare," *Giornale Italiano di Orthopedia e Traumatologia*, vol. XXII, Fascicola 4, pp. 473–483, Dec. 1996.

Boriani et al., "Differential Diagnosis and Surgical Treatment of Primary Benign and Malignant Neoplasms," *The Adult Spine Principles and Practice*, 2nd edition, Chapter 48, pp. 951–987, 1997.

Boriani et al., "La Chirurgia Di Resezione Nel Trattamento Dei Tumori Vertebrali Indicazioni E Limiti," *Aulo Gaggi Editore, Bologna*, II Rachide, pp. 41–52, vol. G.I.S.—Suppl. N, XX/1997.

(List continued on next page.)

*Primary Examiner*—Michael Buiz
*Assistant Examiner*—Julian W. Woo
*Attorney, Agent, or Firm*—Barnes & Thornburg

[57] ABSTRACT

Surgical prosthetic modular devices used singularly or stacked together are provided for use to replace excised vertebral tissue. The devices are rigid plugs, dimensionally similar to normal vertebral bodies, and have ridged faces to engage adjacent vertebral bodies or to interdigitate when stacked. Ridges extend in both the medial/lateral and anterior/posterior directions to prevent slipping in the anterior/posterior and medial/lateral directions respectively. A locking screw may be used to secure a stack to form a singular rigid prosthetic device. The devices are also provided with a plurality of threaded openings. In the method of this invention, a device is used to replace excised vertebral tissue, threaded bolts are inserted into the threaded openings, and other spine stabilization devices are attached to the bolts. In corporectomies, the device can be bolted to a plate, which in turn is fixed to adjacent vertebrae. In spondylectomies, the device can be fixed to a series of posteriorly placed rods.

29 Claims, 6 Drawing Sheets

OTHER PUBLICATIONS

Hart et al., "A System for Surgical Staging and Management of Spine Tumors," *Spine*, vol. 22, pp. 1773–1782, No. 15, 1997.

Boriani et al., "Spine Update: Primary Bone Tumors of the Spine," *Spine*, vol. 22, No. 9, pp. 1036–1044, 1997.

Ciappetta et al., "A Carbon Fiber Reinforced Polymer Cage for Vertebral Body Replacement: Technical Note," *Neurosurgery*, vol. 41, No. 5, pp. 1203–1206, Nov., 1997.

Biagini et al., "Reconstruction techniques in the treatment of vertebral neoplasms," *Chir. Organi Mov.*, LXXXII, 341–355, Oct.–Dec., 1997.

Brochure, *AcroMed Carbon Fiber Interbody Fusion Devices*, Jan., 1998.

Boriani et al., "Resection surgery in the treatment of vertebral tumors," *Chir. Organi Mov.*, LXXXIII, 53–65, 1998.

Biagini et al., "Protesi Vertebrali In Oncologia Orthopedica," *Ciosm*, p. 22, Apr. 1998.

STACKABLE CAGE SYSTEM FOR CORPECTOMY/VERTEBRECTOMY

BACKGROUND AND SUMMARY OF THE INVENTION

This invention relates to inert rigid vertebral prosthetic devices and methods for implanting the devices between adjacent vertebrae to treat or prevent back or neck pain in patients with ruptured or degenerated intervertebral discs and for replacing vertebral bodies damaged by fracture, tumor or degenerative process.

The surgical implant devices and methods of U.S. Pat. Nos. 4,743,256; 4,834,757; and 4,878,915 have greatly improved the success rate and have simplified the surgical techniques in interbody vertebral fusion. In the procedures covered by these patents, biologically acceptable but completely inert bodies are bottomed in channels or grooves of adjoining vertebrae and receive bone ingrowth which quickly fuses the structure to the bone and forms a living bone bridge across the fusion area. The materials and methods which are disclosed in these patents are hereby incorporated by reference.

A more recent invention provides interbody fusion without cutting grooves or channels in the vertebrae and is well suited for anterior cervical and lumbar fusion. The invention of U.S. Pat. No. 5,192,327 provides ring-like prosthetic plugs or discs bottomed on end faces of adjoining vertebrae and constructed and arranged so that they can be used singly or stacked plurally to accommodate individual surgical requirements. These rings can replace excised discs and vertebrae and can also be mounted inside the fibrous disc column connecting adjoining vertebrae. The annular units are oval or partial oval shaped, to conform with vertebral disc shapes, have ridged or peaked surfaces for biting into the vertebrae on which they are seated, for receiving bone ingrowth in valleys between the peaks, and for interdigitating when stacked. The open central portion of the ring is preferably packed with bone graft or other osteobiologic materials to facilitate bone ingrowth. The methods and materials disclosed in the '327 patent are hereby incorporated by reference.

The present invention includes a plurality of inert rigid vertebral prosthetic devices ("cages") and methods for use. Each of these cages is a generally rectangular shaped body, conforming in shape and size with the hard end plates of the vertebrae on which the prosthetic device is to be seated. Each of the cages has ridged surfaces for gripping the vertebrae to resist expulsion, forming valleys to facilitate bone ingrowth, and interdigitating with adjacent cages for stacking. The cages of the current invention have ridges which run in both the anterior/posterior and medial/lateral directions respectively. Such ridges prevent slipping in the medial/lateral and anterior/posterior directions, whether implanted singly or stacked with other cages of this invention. Also, the anterior/posterior and medial/lateral ridges intersect in the corners of the surfaces to produce a crisscross pattern, which further resists rotation or other torsional type forces.

Also, each cage is provided with a plurality of threaded openings in the side walls. While it is known in the art to provide an opening for use with an insertion tool, this invention includes a plurality of additional threaded openings, at various locations around the side walls. These threaded openings are positioned and sized to receive threaded components of other spine stabilization devices. For example, in corpectomies or vertebrectomies, an anterolateral plate or rod system could be anchored to the cage by threading a connecting screw into a laterally placed hole, and the plate or rods could then be secured to adjacent vertebrae. Similarly, the cages could be used in conjunction with posterior spinal rods or plate systems. Examples of such plates and rod systems are disclosed in U.S. Pat. Nos. 4,696,290; 5,261,910; 4,887,595; 5,217,461; and 5,257,993. When posterior spinal rods are used, the connecting screws which connect the cage with the posterior osteosynthetic system act as true artificial pedicles. The devices and methods disclosed in the above cited patents are hereby incorporated by reference.

The invention comprises a set of cages of various sizes. The cages are provided in various heights for use individually. Also, several cages may be stacked to produce a prosthetic device of appropriate height to meet specific surgical demands. The ridges of the stacked cages interdigitate, and a locking screw and nut may be used to secure the stack to produce a singular rigid prosthetic device. Recesses in the ridged faces of the cages allow the locking screw to be sized such that the screw does not extend beyond the top and bottom surfaces of the stack. Thus, the screw does not interfere with placement of the stack into the vertebral column, and it does not assume any axial loading from adjacent vertebrae. Also, smaller cages may be used to replace partially damaged discs, or a stack of smaller cages may be used when vertebrae are partially excised. Additionally, wedge-shaped cages are provided for surgical applications where anatomical curvature is needed. By providing such a variety, the surgeon can choose the proper combination of cages to accommodate a myriad of different surgical situations.

The cages are preferably made of radiolucent materials such as a carbon fiber reinforced high temperature thermoplastic. Preferred polymers are polyether ether ketone, polyether ketone ketone, polyether ketone ether ketone ketone, and carbon fiber reinforced polyether ketone ether ketone ketone. Additionally, polycarbonate, polyprophylene, polyethylene, polysulfone, and polyphenylsulfone type plastic material filled with glass or carbon fibers can be used. Other orthopaedic implant materials such as stainless steel, titanium, and cobalt-chromium alloys may be used.

The invention further comprises a method of use. In this method, the vertebral column is prepared to receive the prosthetic device, a stack of at least one of the cages is formed to fit into the vertebral column, graft material is placed within an aperture in the stack, and the stack is inserted into the vertebral column. Following insertion, one or more connecting screws may be used to secure the stack to other spinal stabilization devices, such as plates or rods.

DETAILED DESCRIPTION OF THE DRAWINGS

Figure 1:
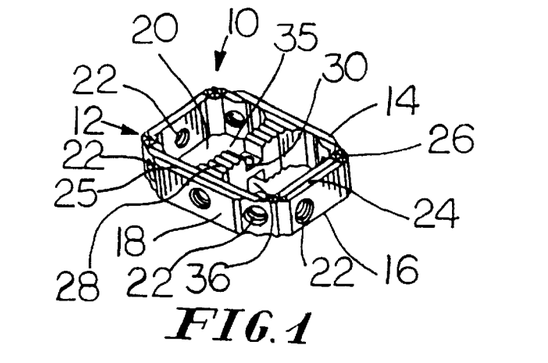
FIG. 1 is a top and side perspective of a prosthetic device of this invention.

In FIG. 1, the reference numeral 10 designates generally a prosthetic device of this invention, composed of a rigid biologically acceptable and inactive material, preferably a radiolucent plastic material, inert metal, and the like. The device 10 is a generally rectangular body 12 which is shaped and sized to conform with the disc space between adjoining vertebrae in a vertebral column. The body 12 has a top face 14 and a bottom face 16 and side walls 18 therebetween. The side walls 18 define an aperture 20 which extends through the top and bottom faces 14, 16.

Figure 2:
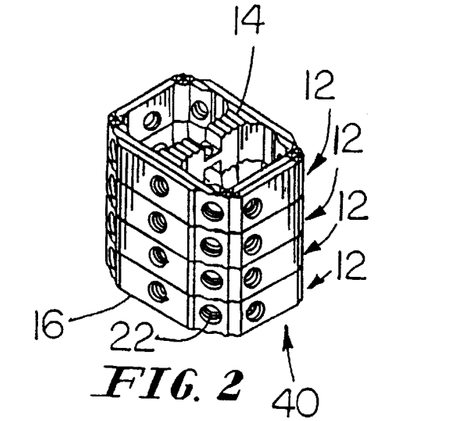
FIG. 2 is a top and side perspective of a stack of prosthetic devices in stacked relation.

Ridges 24, 25 are provided on the top and bottom faces 14, 16. Ridges 24 run generally in the anterior/posterior direction and ridges 25 run generally in the medial/lateral direction, and they meet in the corners to form a crisscross pattern 26. The ridges 24, 25 are designed to interdigitate to form a stack 40, as shown in FIG. 2. The ridges 24, 25 are also designed to bite into the vertebrae on which the device is to be seated. The anterior/posterior ridges 24 provide stability from movement in the medial/lateral direction, and the medial/lateral ridges 25 provide stability from movement in the anterior/posterior direction.

Body 12 also is provided with a fastener opening 30. As shown in FIG. 1, an integral cross bar 28 bisects the aperture 20, and the fastener opening 30 extends through the cross bar 28. Also, as shown, recesses 35 and 36 are provided so that the fastener opening 30 is recessed from the top and bottom faces 14, 16. A plurality of threaded openings 22 are provided in the side walls 18, to allow for attachment to other spine stabilization devices.

FIG. 2 shows a stack 40 of bodies 12. The ridges 24, 25 of the adjacent bodies 12 have been allowed to interdigitate. Such a stack 40 can be created to replace a vertebral body, with the size of the stack conforming with the open vertebral space.

Figures 3, 4, 5:
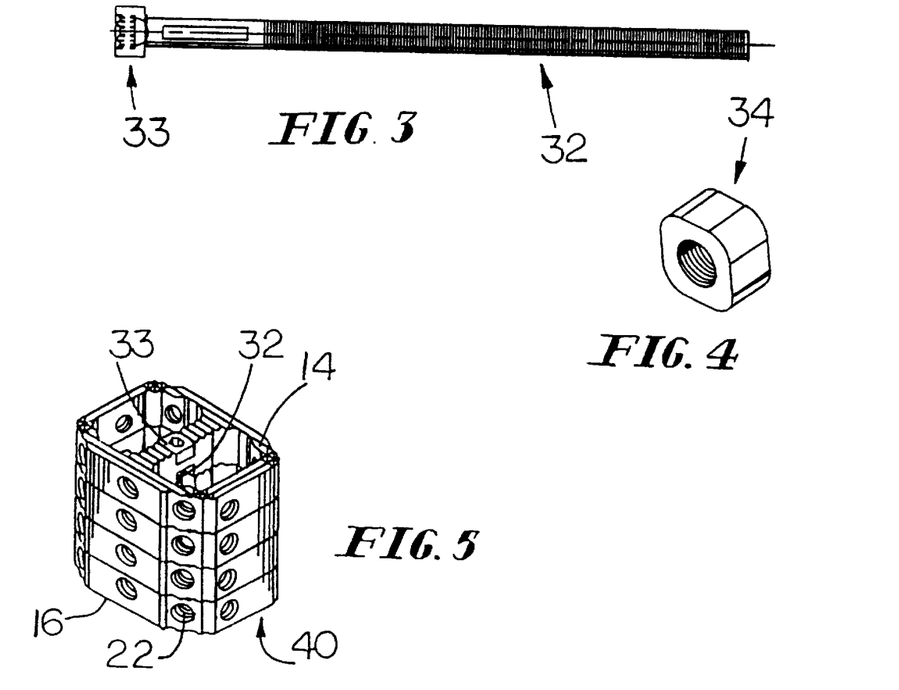
FIG. 3 is a side perspective of a locking screw.
FIG. 4 is a top and side perspective of a locking nut.
FIG. 5 is a view similar to FIG. 2, but showing the locking screw in place.

FIGS. 3 and 4 show a locking screw 32 and locking nut 34 which can be used to secure the stack 40. The head 33 of the locking screw 32 and the locking nut 34 are sized to fit within the recesses 35 and 36. The locking screw 32 is sized such that it can extend through the fastener opening 30 of the stack 40, without extending beyond the top face 14 at the top of the stack 40 and the bottom face 16 at the bottom of the stack 40. FIG. 5 shows the stack 40 with the locking screw in place.

Figure 6:
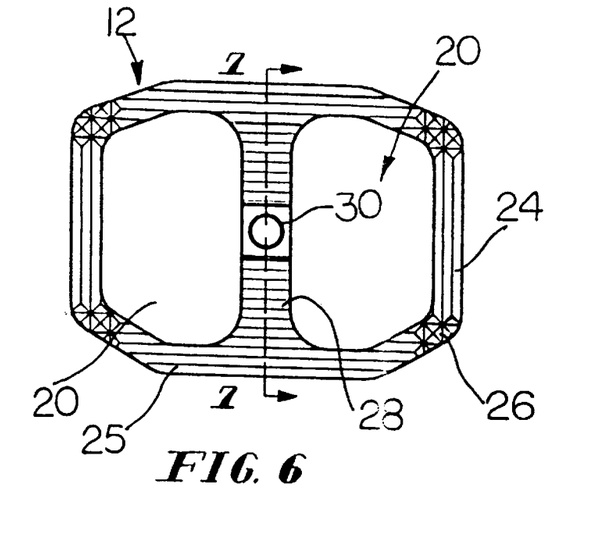
FIG. 6 is a top view of the device of FIG. 1.
Figure 7:
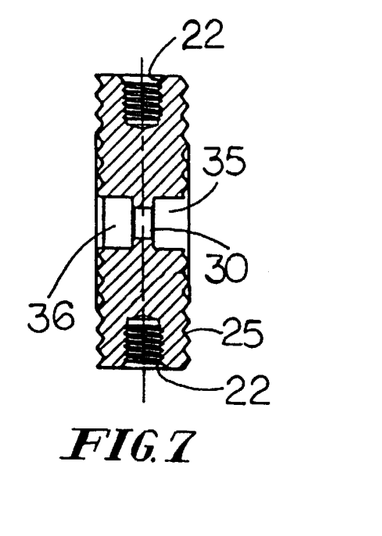
FIG. 7 is a sectional view along the line of 7—7 of FIG. 6.

FIGS. 6–9 illustrate the features of the body 12. FIG. 6 is a top view of the body 12, showing the anterior/posterior and medial/lateral grooves 24, 25, the crisscross pattern 26, the cross bar 28, and the fastener opening 30. The aperture 20, which has been bisected by the cross bar 28, can be packed with bone graft material such as bone fragments or other osteobiologic materials. Such bone fragments can be harvested from the iliac crests of the patient's pelvic bones or from the patient's ribs. FIG. 7, a sectional view along line 7—7 of FIG. 6, shows the recesses 35 and 36, which are designed to receive the locking screw 32 and locking nut 34 and the fastener opening 30 passing through. FIG. 7 also illustrates the location of two of the threaded openings 22.

Figure 8:
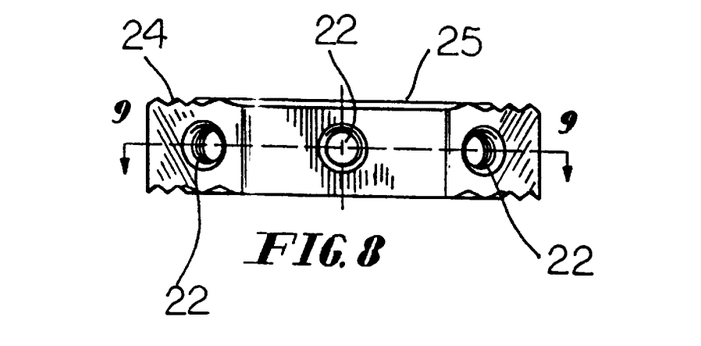
FIG. 8 is a side view of the device, showing three threaded openings.
Figure 9:
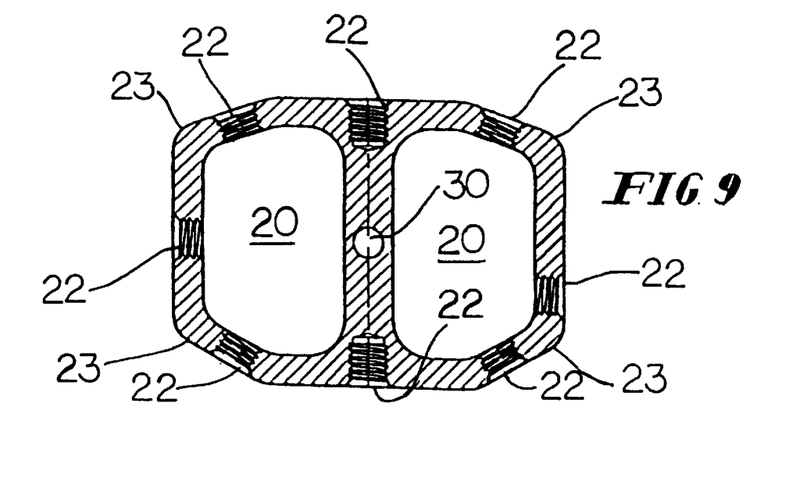
FIG. 9 is a sectional view along the line 9—9 of FIG. 8.

FIGS. 8 and 9 show the location of the threaded openings 22 in the illustrated embodiment. FIG. 8 is a front view, showing three of the openings 22, and FIG. 9 is a sectional view along line 9—9, showing the placement of the eight threaded openings 22 of the illustrated embodiment. As can be seen in FIG. 9, the threaded openings 22 are provided in various locations along the side walls 18 to enable a wide variety of applications. Beveled corners 23 of various angles allow the threaded openings 22 to be placed at a multitude of different angles, thus increasing the likelihood that the device will have a threaded opening 22 which is at the angle necessary for a specific application.

Figure 10:
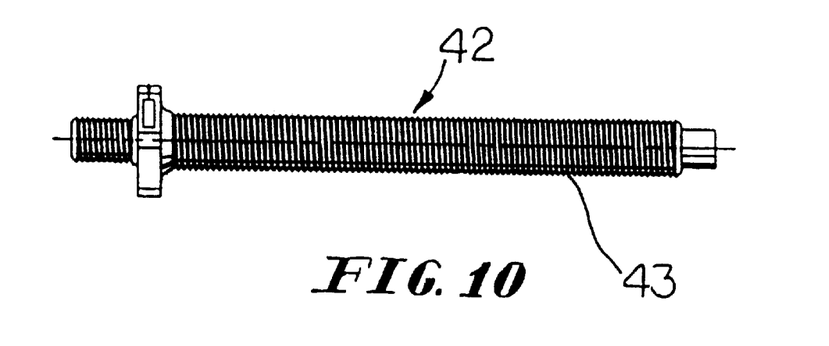
FIG. 10 is a side view of a connecting screw for attaching additional spinal stabilization devices.
Figure 11:
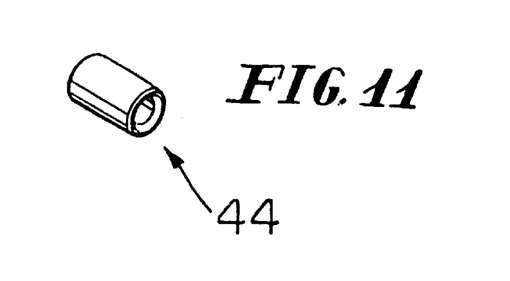
FIG. 11 is a protective sleeve for covering the threaded portion of the connecting screw.
Figure 12:
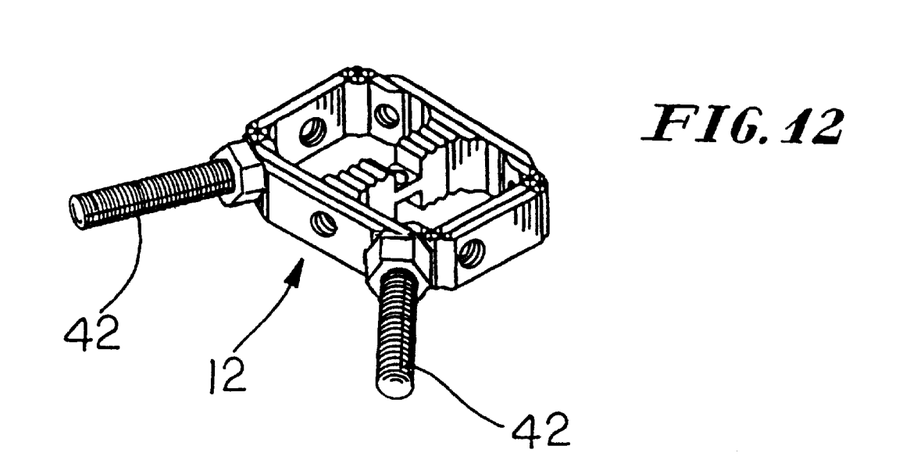
FIG. 12 is similar to FIG. 6, except that it shows several connecting screws threaded into the device.

FIG. 10 is an example of a connecting screw 42 which is designed to thread into one of the threaded openings 22 of the device 10. Examples of screws of this type are disclosed in U.S. Pat. No. 5,261,910, incorporated herein by reference. FIG. 11 shows a protective sleeve 44 which may be placed over the threads 43 of the connecting screw 42, to protect soft tissue. FIG. 12 shows the body 12, with two connecting screws 42 threaded into several of the threaded openings. Such a configuration may be used in corpectomies or vertebrectomies.

Figure 13:
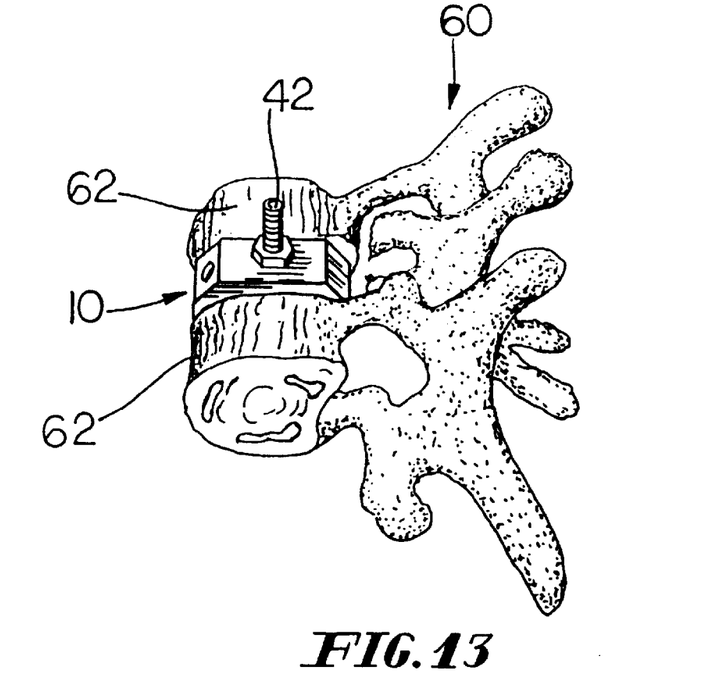
FIG. 13 shows the device after insertion into a vertebral column following corpectomy.
Figure 14:
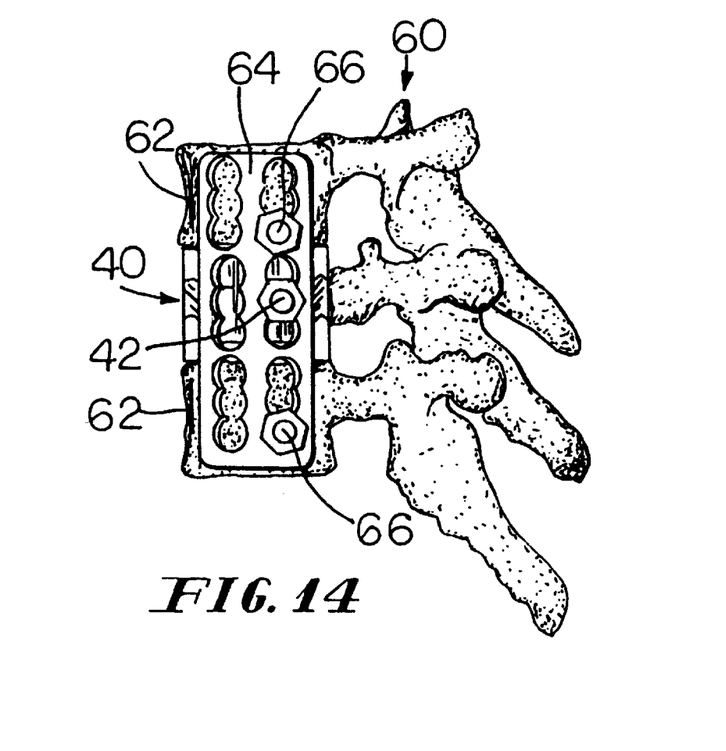
FIG. 14 is similar to FIG. 13 except that it shows a plate attached to the device and the plate is screwed into adjacent vertebrae.

FIGS. 13 and 14 illustrate the method of this invention following a corpectomy. FIG. 13 shows body 12 after insertion into a vertebral column 60 following a corpectomy. A connecting screw 42 extends from one of the threaded openings 22. FIG. 14 shows a stack 40, which has been inserted into a vertebral column 60. As with the body 12 in FIG. 13, a connecting screw 42 extends from one of the threaded openings 22 of stack 40. A plate 64 has been inserted over the connecting screw 42 and has been fixed to several adjacent vertebrae 62 by use of standard bone screws 66. The plate may be of the type disclosed in U.S. Pat. Nos. 4,696,290 and 5,261,910, also incorporated herein by reference. It should be understood that a single body 12 or stack 40 could be used to fill disc and vertebral body space, depending on the geometry of the individual patient.

Figure 15:
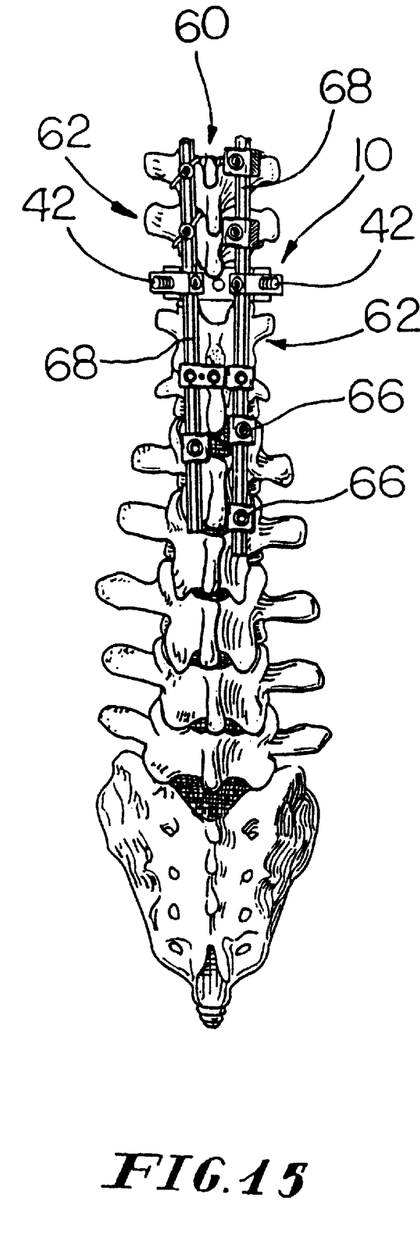
FIG. 15 shows the device connected to spinal rods, as used in vertebrectomies.

The prosthetic device 10 of this invention could also be used for vertebral reconstruction and fixation following vertebrectomies, as shown in FIG. 15. As illustrated, such surgeries would involve a construct such as the one illustrated in FIG. 12. Spinal rods 68 would be fixed to the vertebral column 60 using standard techniques. Then, following vertebrectomy, a body 12 and several connecting screws 42 are used to replace the excised vertebral tissue. The connecting screws 42 are then secured to the spinal rods 68. Rods of the type disclosed in U.S. Pat. Nos. 4,887,595 and 5,217,461 may be used, which are incorporated herein by reference. As illustrated, the connecting screws 42 act as artificial pedicles.

Figure 16:
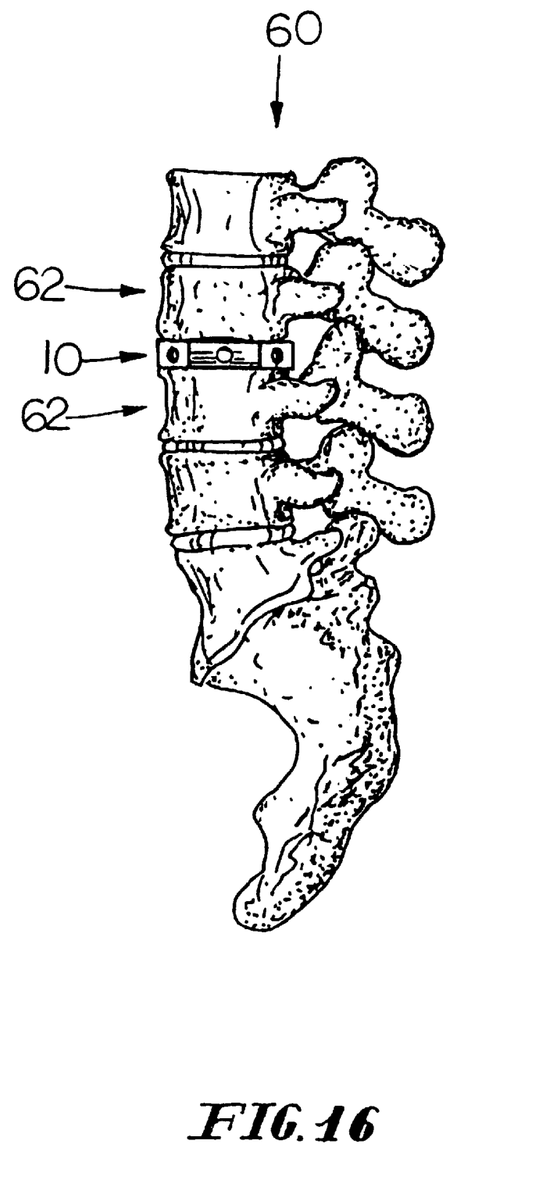
FIG. 16 shows the device inserted into a spinal column following excision of disc material.

In the above illustrated reconstructions, the prosthetic device 10 of this invention has been fixed to additional spine stabilization devices. However, it should be noted that because the ridges 24, 25 are designed to bite into the adjacent vertebrae 62, the prosthetic device of this invention may not require screws or other fixation devices to anchor the prosthetic device 10 to the vertebrae. As seen in FIG. 16, a single body 12 could be used for disc replacement without use of screws. Also, it should be understood that the above uses are provided for illustrative purposes. Other reconstructions using the device of this invention employing other spine stabilization devices are within the scope of this invention.

Figure 17:
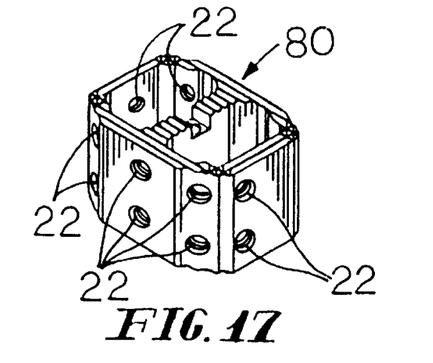
FIG. 17 is a top and side perspective of a tall device.

Because surgical needs vary from patient to patient, the body 12 would be provided in a variety of sizes. Ideally, for lumbar use, the body 12 would measure 30 mm×40 mm, and it would be available in various heights, for example, of 9, 12, and 24 mm. The 9 and 12 mm high devices could appear as illustrated in FIG. 1, and the 24 mm tall body 80 could be provided with an additional row of threaded openings 22, as seen in FIG. 17. Also, for thoracic applications, a medium body of the same configuration as shown in FIG. 1 could be provided. Such a device ideally would measure 20 mm×30 mm and would be available in the same heights as the 30 mm×40 mm body 12.

Figure 18:
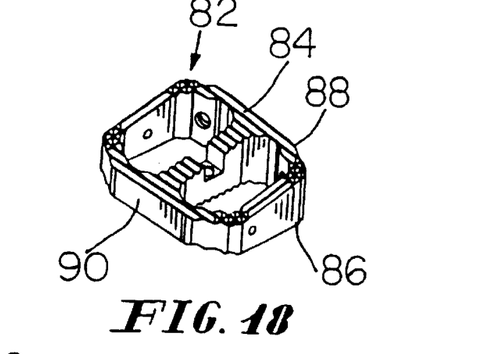
FIG. 18 is a top and side perspective of a wedge shaped device.
Figures 19, 20, 21:
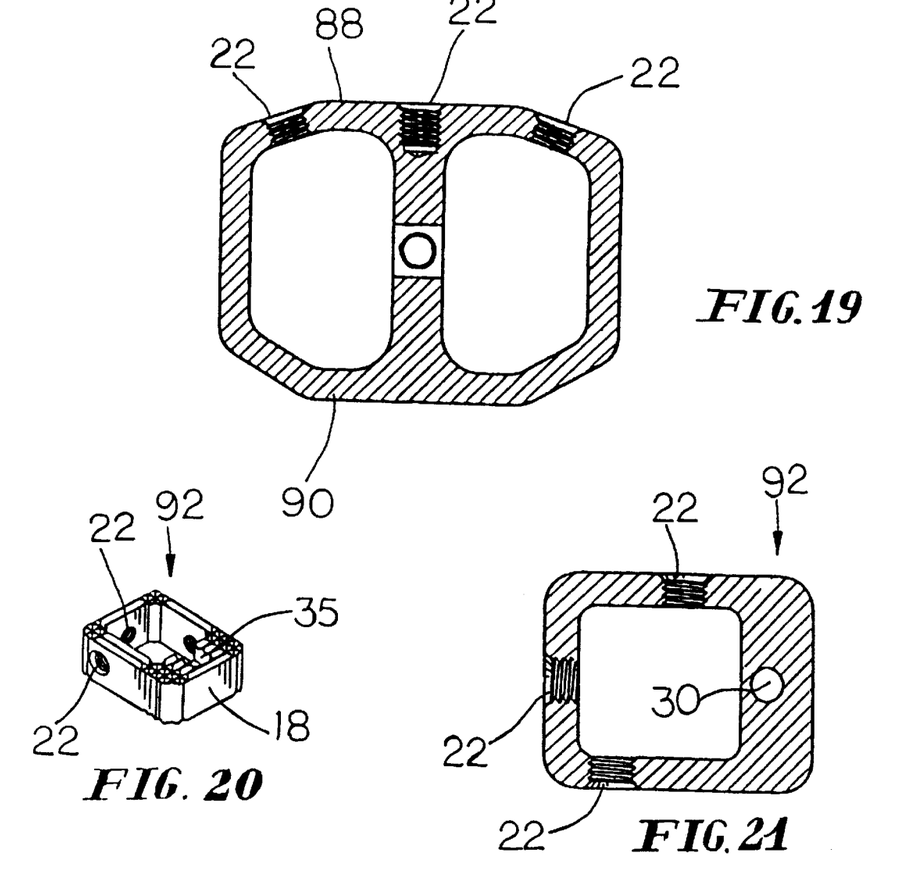
FIG. 19 is similar to FIG. 9, except that it is a sectional view of a wedge shaped device.
FIG. 20 is a top and side perspective of a small device.
FIG. 21 is similar to FIG. 9, except that it is a sectional view of a small device.

Various applications may require other shapes and sizes of the device 10 of this invention. A wedge-shaped body 82 is illustrated in FIG. 18. It is tapered to be thicker at its first end 88 than at its second end 90. The wedge-shaped body 82 has ridged top and bottom faces 84 and 86 similar to those of the body 12, and are designed to interdigitate with the top and bottom faces 14, 16 of the body 12. By way of example, the wedge-shaped body 82 may taper at an angle of 11° from its first end 88 to its second end 90. Such wedge-shaped bodies 82 would suit surgical applications where the space between adjacent vertebrae is wider at one end than the other or where anatomical curvature needs to be corrected, reproduced or created. As shown in FIG. 19, the threaded openings 22 may be provided on the first end 88 only, due to the reduced height of the second end 90.

Finally, a small body 92 could be provided for surgical applications in which only a portion of a vertebral body is involved. As illustrated in FIGS. 20 and 21, the small body 92 has all of the features of the body 12, except that the small body 92 does not have a cross bar 28. Correspondingly, the recesses 35 and 36 and fastener opening 30 have been moved closer to a side wall 18. Also, because of size limitations, the number of threaded openings 22 has been reduced. Such a small body 92 could measure 20 mm×25 mm, while an extra-small body of the same configuration could measure 15 mm×20 mm. These small and extra-small bodies could be provided in a variety of heights, similar to the larger bodies described above. Other shapes and sizes may be provided while remaining within the scope of this invention.

The following operative procedure may be used. Surgical removal of vertebral tissue is performed according to standard techniques. The surgeon selects the appropriate combination of prosthetic devices 10 to be inserted into the vertebral column 60. If more than one device 10 is used to form a stack 40, the stack 40 is secured with a locking screw 32 to form a rigid prosthetic device. Alternatively, a singular body 10 may be used as the prosthetic device. The aperture 20 may then be packed with graft material, often bone fragments. The prosthetic device is then inserted into the vertebral column 60 using tools which are known in the art.

If the excised vertebral tissue is the body portion of a vertebra, the inserted prosthetic device may then be secured to a plate 64, which in turn can be fixed to adjacent vertebrae 62. If the surgery involved a vertebrectomy, attachment to rods 60, which had already been placed in the vertebral column 60 during a posterior procedure, may be appropriate. Individual circumstances may require use of other spine stabilization devices, or a combination of such devices. It should be understood that the procedures described herein are for illustrative purposes, and that use of the prosthetic device of this invention in conjunction with other spine stabilization devices is within the scope of this invention. Ideally, the threaded openings 22 would be sized to engage any fixation device which accepts a 4 mm screw.

What is claimed is:

1. A prosthetic device to integrate with and support vertebrae in a vertebral column, comprising:

a plurality of inert bodies conforming in shape and size with hard end plates of vertebrae on which the prosthetic device is to be seated, each of the bodies having ridged top and bottom faces adapted to selectively interdigitate with faces of adjacent bodies and to bite into adjoining vertebrae, the ridged top and bottom faces having anterior/posterior and medial/lateral ridges to provide stability in the medial/lateral and anterior/posterior directions respectively, each of the bodies also having side walls disposed between the ridged top and bottom faces to define an aperture which opens through the faces, and a plurality of threaded openings disposed within the side walls, said plurality of threaded openings positioned and designed to receive threaded components of additional spine stabilization devices.

2. The device of claim 1, further comprising a fastener opening positioned through the top and bottom faces and extending generally in the same direction as the vertebral column, the fastener opening positioned to receive a fastener to secure a stack of the bodies.

3. The device of claim 2, wherein the fastener opening is further defined by recesses in the ridged top and bottom faces and a passageway extending there between.

4. The device of claim 3, wherein the fastener comprises a locking screw and is sized such that it does not protrude beyond the stack of bodies.

5. The device of claim 1, wherein the threaded component is a connecting screw and the device further comprises a protective sleeve to cover an end of the connecting screw.

6. The device of claim 1, wherein the anterior/posterior and medial/lateral ridges intersect to form a crisscross pattern.

7. The device of claim 1, wherein the device is comprised of radiolucent material.

8. The device of claim 7, wherein the radiolucent material comprises a carbon fiber reinforced polymer.

9. A prosthetic device for vertebral fusion, comprising: a plurality of inert bodies conforming in shape and size with hard end plates of vertebrae on which the prosthetic device is to be seated, each of said bodies having ridged top and bottom faces adapted to selectively interdigitate with faces of adjacent bodies to form a stack and to bite into adjoining vertebrae, the ridged top and bottom faces having anterior/posterior and medial/lateral ridges to provide stability in the medial/lateral and anterior/posterior directions respectively, side walls disposed between the ridged top and bottom faces to define an aperture which opens through the faces, and a fastener opening extending from the top face to the bottom face and extending through each body generally in the same direction as the vertebral column but recessed from the top and bottom faces, the fastener opening positioned to receive a fastener therein, and the fastener is sized to secure the stack of bodies without protruding from the stack.

10. A device of claim 9 wherein the fastener comprises a locking screw.

11. A prosthetic device adapted for fusing together adjoining vertebrae, comprising:

an inert body conforming in shape and size with hard end plates of vertebrae on which the prosthetic device is to be seated, the body having ridged top and bottom faces, side walls disposed between the ridged top and bottom faces, the side walls having a plurality of beveled corners defining a plurality of side faces at varying angles to each other and a plurality of threaded openings disposed within the side faces, said plurality of threaded openings positioned and designed to receive threaded components of an additional spine stabilization device.

12. A device of claim 11 wherein the additional spine stabilization device comprises an anterior plate or rod system.

13. A device of claim 11 wherein the additional spine stabilization device comprises a posterior rod or plate system.

14. A method of vertebral fusion comprising the steps of providing a plurality of inert bodies shaped to fit opposed end faces of vertebrae in a vertebral column, each of the bodies having ridged top and bottom faces adapted to selectively interdigitate with faces of adjacent bodies to form a stack and to bite into adjoining vertebrae, the ridged top and bottom faces having anterior/posterior and medial/lateral ridges to provide stability in the medial/lateral and anterior/posterior directions respectively, each of the bodies also having side walls disposed between the ridged top and bottom faces to define an aperture which opens through the faces, and each of the bodies having a fastener opening extending through each body from the top face to the bottom face and extending generally in the same direction as the vertebral column, selecting the appropriate combination of bodies for fusion within the vertebral column, stacking the appropriate combination of bodies by allowing the ridged top and bottom faces of adjacent bodies to interdigitate, providing a fastener, fastening the stacked bodies by extending the fastener through the fastener opening in each of the bodies to form a rigid prosthetic device, preparing the vertebral column to receive the rigid prosthetic device, and inserting the rigid prosthetic device into the vertebral column.

15. The method of claim 14 wherein the fastener opening is further defined by recesses in the ridged top and bottom faces and extends there between, and the fastener is sized such that it does not protrude from the rigid prosthetic device.

16. The method of claim 15 wherein the fastener comprises a locking screw.

17. The method of claim 14 wherein each of the bodies further comprises a plurality of threaded openings disposed within the side walls, and the method further comprises the steps of providing an additional spine stabilization device, including a threaded component thereof, and threading the threaded component into one of the threaded openings disposed within the side walls.

18. The method of claim 14, further comprising the step of placing bone graft material in the aperture prior to inserting the rigid prosthetic device into the vertebral column.

19. A method of vertebral fusion comprising the steps of providing a plurality of inert bodies shaped to fit opposed end faces of vertebrae in a vertebral column, each of the bodies having ridged top and bottom faces adapted to bite into adjoining vertebrae, the ridged top and bottom faces having anterior/posterior and medial/lateral ridges to provide stability in the medial/lateral and anterior/posterior directions respectively, each of the bodies also having side walls disposed between the ridged top and bottom faces to define an aperture which opens through the faces, and a plurality of openings disposed within the side walls, preparing a stack of at least one of the bodies, preparing the vertebral column to receive the stack, inserting the stack into the vertebral column, providing an additional spine stabilization device, and attaching the additional spine stabilization device to one of the openings disposed within the side walls.

20. The method of claim 19 wherein the plurality of openings disposed within the side walls are threaded.

21. The method of claim 20 wherein the additional spine stabilization device includes a plate and a screw, the step of preparing the vertebral column to receive the stack includes performing a corpectomy, the attaching step involves extending the screw through an opening in the plate and threading the screw into one of the openings disposed within the side walls, and the method includes the additional step of securing the plate to a vertebra.

22. The method of claim 20 wherein the additional spine stabilization device includes a rod and a screw, the step of preparing the vertebral column to receive the stack includes performing a vertebrectomy, the attaching step involves securing the rod to the stack by threading the screw into one of the openings disposed within the side walls, and the method includes the additional step of securing the rod to the vertebral column in a location distinct from the stack.

23. The device of claim 10 wherein the side walls further comprise a plurality of corners defining a plurality of side faces at a variety of angles to each other, the side walls further comprising a plurality of threaded openings designed to receive threaded components of an additional spine stabilization device, and positioned in a variety of angles to enable a custom fit.

24. A prosthetic device to integrate with and support vertebrae in a vertebral column, comprising:

a plurality of inert bodies conforming in shape and size with hard end plates of vertebrae on which the prosthetic device is to be seated, each of the bodies having ridged top and bottom faces adapted to selectively interdigitate with faces of adjacent bodies and to bite into adjoining vertebrae, the ridged top and bottom faces having anterior/posterior and medial/lateral ridges to provide stability in the medial/lateral and anterior/posterior directions respectively, each of the top and bottom faces having recesses therein, and each of the bodies having a fastener opening extending generally in the same direction as the vertebral column from the recess in the top face to the recess in the bottom face, the fastener opening positioned to receive a locking screw to secure a stack of the bodies, the locking screw sized such that it does not protrude beyond the stack of bodies, each of the bodies also having side walls disposed between the ridged top and bottom faces to define an aperture which opens through the faces, and a plurality of threaded openings disposed within the side walls, said plurality of threaded openings positioned and designed to receive threaded components of additional spine stabilization devices.

25. The device of claim 24, further comprising a protective sleeve to cover an end of the connecting screw.

26. The device of claim 24, wherein the anterior/posterior and medial/lateral ridges intersect to form a crisscross pattern.

27. The device of claim 24, wherein the device is comprised of radiolucent material.

28. The device of claim 27, wherein the radiolucent material comprises a carbon fiber reinforced polymer.

29. The device of claim 24 wherein the side walls further comprise a plurality of corners defining a plurality of side faces at a variety of angles to each other and the threaded openings are located on the side faces and positioned in a variety of angles to better accommodate the additional spine stabilization devices.

* * * * *